United States Patent [19]

Ponlot et al.

[11] 4,203,463
[45] May 20, 1980

[54] FLOW-REGULATING DEVICE FOR PERFUSION-TRANSFUSION APPARATUS

[76] Inventors: Victor Ponlot; Jacques Ponlot, both of 2, Rue Saint Marceaux, Paris 17, France

[21] Appl. No.: 894,618

[22] Filed: Apr. 6, 1978

[30] Foreign Application Priority Data

Apr. 8, 1977 [FR] France .............................. 77 10711

[51] Int. Cl.² .......................................... F16K 21/16
[52] U.S. Cl. .............................. 137/403; 128/214 C; 137/433; 73/309
[58] Field of Search ............ 128/214 R, 214 C, 214.2; 137/429, 430, 433, 437, 403; 73/209, 309

[56] References Cited

U.S. PATENT DOCUMENTS

| | | | |
|---|---|---|---|
| 538,802 | 5/1895 | Sullivan | 137/437 |
| 1,606,274 | 11/1926 | Utley | 137/437 |
| 2,367,951 | 1/1945 | Lewis et al. | 137/437 |
| 2,675,000 | 4/1954 | Ford | 128/214 C |
| 2,844,147 | 7/1958 | Beacham | 137/433 |
| 2,879,784 | 3/1959 | Cutter | 128/214 C |
| 3,049,918 | 8/1962 | Sparkuhl | 28/214 C |
| 3,101,570 | 8/1963 | Lienard | 137/433 |
| 3,207,372 | 9/1965 | Evans | 128/214 C |
| 3,351,083 | 11/1967 | Sait | 137/433 |
| 3,495,617 | 2/1970 | Zifferer | 137/433 |
| 3,785,378 | 1/1974 | Stewart | 128/214 C |
| 3,963,024 | 6/1976 | Goldowsky | 128/214 C |
| 4,096,879 | 6/1978 | Serur et al. | 137/433 |

*Primary Examiner*—Martin P. Schwadron
*Assistant Examiner*—G. L. Walton
*Attorney, Agent, or Firm*—Haseltine, Lake & Waters

[57] ABSTRACT

A so-called "visual" flow-regulation system ensuring a constant flow-rate and presenting an impenetrable barrier to air-bubbles even after completion of the perfusion, the system comprising a central tube on which a sleeve is arranged to slide, the sleeve being provided with a float and further comprising a flexible diaphragm intended to cooperate with the extremity of the fixed central tube, the unit imparting to the liquid passing through it a downward and then an upward movement.

11 Claims, 5 Drawing Figures

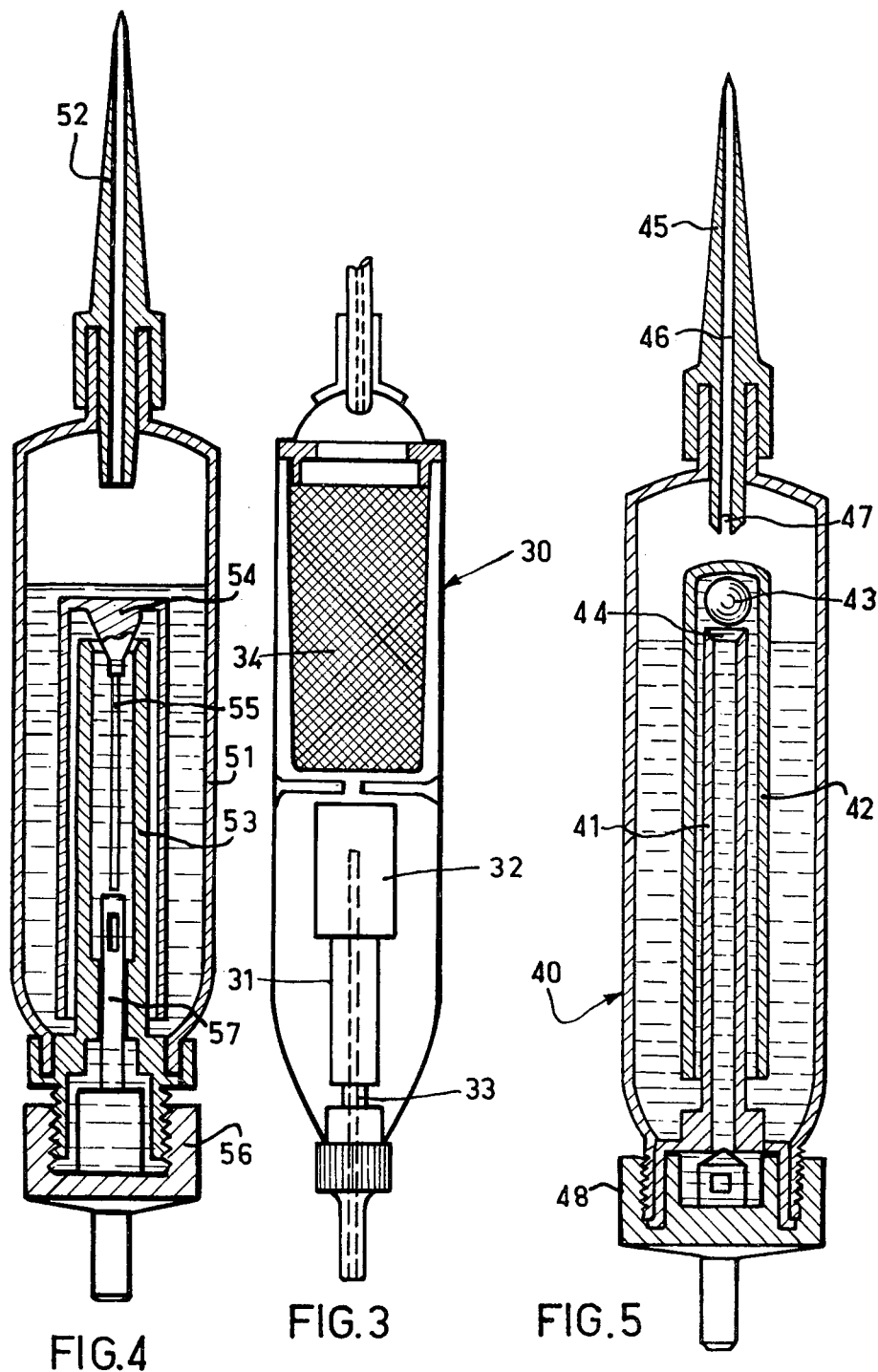

FLOW-REGULATING DEVICE FOR PERFUSION-TRANSFUSION APPARATUS

BACKGROUND

The present invention relates to a flow-regulating device for medical apparatus known generally as perfusion-transfusion apparatus, the device serving additionally to provide an impenetrable anti-air-bubble barrier, even after the perfusion is finished.

The apparatus at present employed for intravenous administration of biological serums contained in receptacles have various disadvantages, in particular irregular flow of the liquid to be transfused, and the passage, at the end of the perfusion, of an air-bubble liable to result in injury to the patient, which compels the hospital staff to supervise very closely the regulating device, commonly known as a "visual" apparatus because it is made of transparent synthetic material which enables the flow to be observed.

SUMMARY OF THE INVENTION

An object of the present invention is to provide a flow-regulating system commonly known as a "visual system", ensuring a constant flow-rate and presenting an impenetrable barrier to air-bubbles, even after completion of the perfusion.

The device according to the invention is constituted by a chamber of transparent synthetic material forming the visual device, the upper portion of which is provided with a perforating device, characterized in that it comprises a fixed central tube around which is a cylindrical sleeve, provided with a float, a flexible diaphragm intended to cooperate with the extremity of the fixed central tube so as to ensure perfect fluid-tightness if so desired, its lower portion cooperating as required with the foot of the fixed central tube forming a seating intended to provide a second fluid-tight joint, a cavity being furthermore provided at the upper extremity of the sleeve, above the flexible diaphragm, the sleeve being formed in such manner that there exists an annular passage between the fixed central tube and said sleeve.

The lower part of the visual device comprises a threaded outlet orifice into which the central tube discharges and on which it is possible to fit a micro-regulation system for the flow of liquid.

The essential feature of the apparatus of the invention is not to permit the passage of any air-bubble, even at the end of the perfusion, by virtue of either of the fluid-tightness joints or of both simultaneously, by forcing the perfused liquid to circulate at one moment from the top to the bottom and at a second moment from the bottom to the top before being discharged from the fixed central tube.

The invention will be more clearly understood from a study of the description which follows below of preferred embodiments of the invention, and from an examination of the accompanying drawing.

BRIEF DESCRIPTION OF THE VIEWS OF THE DRAWINGS

FIG. 3 is an elevational sectional view of an alternative form of the visual device of FIG. 1.

FIG. 4 is a longitudinal sectional view of another alternative embodiment of that of FIG. 1.

FIG. 5 is a longitudinal sectional view of another alternative form of embodiment of the invention.

DETAILED DESCRIPTION

Figure 1:
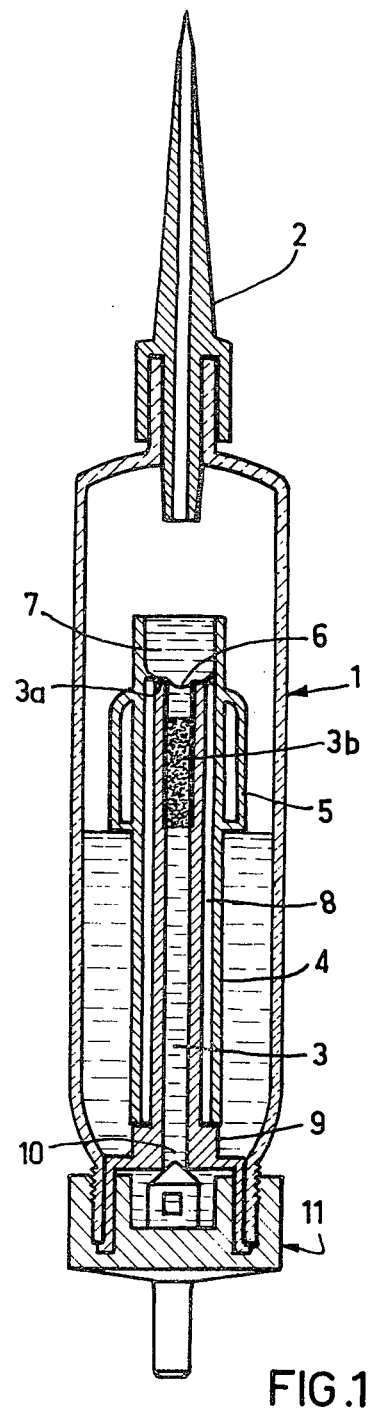
FIG. 1 is a longitudinal sectional view of a "visual" device according to the invention.

Referring now to FIG. 1, there is shown a visual apparatus according to the invention, constituted by a chamber 1 of transparent material, comprising a perforating device 2 at its upper portion. Inside the chamber 1 is arranged a fixed central tube 3 on which a sleeve 4 slides freely. This sleeve 4 is provided at ⅔ rds of its height with a float 5, constituted by a circular skirt. The upper portion of the sleeve comprises a very flexible diaphragm 6 cooperating with the upper extremity 3a of the fixed tube 3, a cup 7 being provided above the diaphragm 6.

An annular passage 8 is provided around the central tube down to the foot 9 of the tube. At the lower part of the visual apparatus there is secured at the outlet 10 of the tube 3 a micro-adjustment device 11. The tube 3 is provided with a filter 3b.

The visual apparatus according to the invention operates in the following manner:

The serum flows through the passage in the perforator 2 and falls first at all into the cup 7 which fills and has the object of weighting the sleeve and float unit to ensure rapid closure when the perfusion is interrupted. The serum then fills the chamber 1 and reaches the float 5 which has the effect of lifting the sleeve 4 and removing the diaphragm 6 from the extremity 3a of the central tube 3, thus opening the annular passage 8. As the lower extremity of the sleeve 4 is no longer in contact with the foot 9 of the tube 3, the serum then passes through the annular channel 8 and through the tube 3 and the filter 3b finishing at the end 10 and the micro-adjustment device 11.

The apparatus being primed, the serum flows, and it is clear that no air-bubbles can pass since they must pass through the annular channel 8 and the tube 3. When the serum is finished, the sleeve 4 moves down again and the flexible diaphragm 6 sticks or, if preferred, is sucked against the extremity 3a of the tube 3, thus hermetically closing the passage against any air-bubble, and this effect is obtained before the serum is exhausted from the visual apparatus, especially since the lower part of the sleeve 4 then cooperates with the foot 9 of the tube 3 which forms a seat and also closes the annular passage 8.

An absolute double fluid-tight closure is thus obtained. The circuit traversed by the liquid goes from the top to the bottom and then from the bottom to the top.

Figure 2:
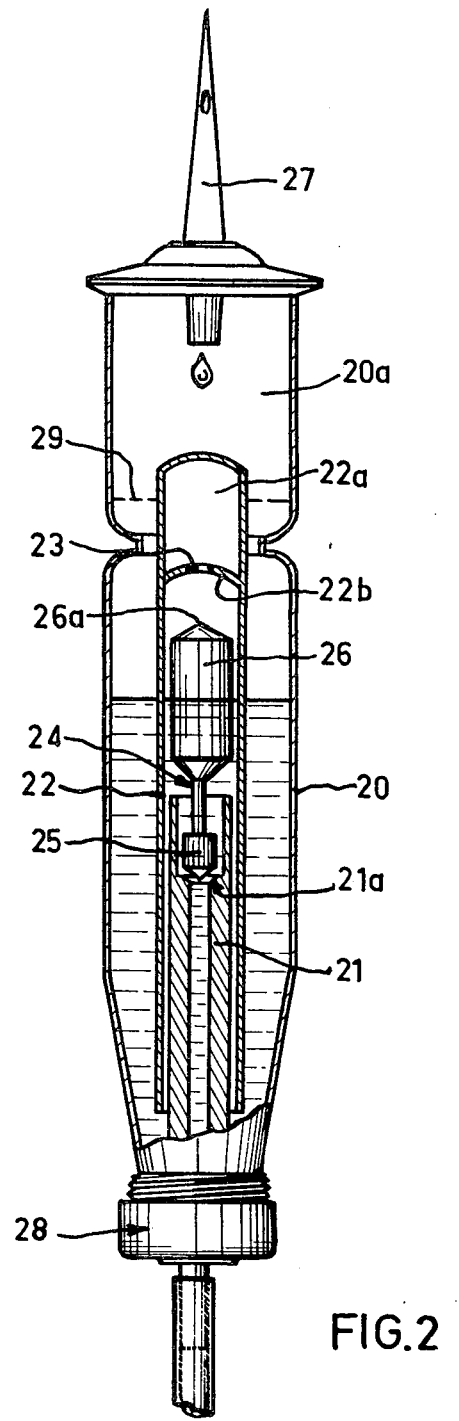
FIG. 2 is a partly broken away view, in section, of a visual device according to the invention comprising two super-imposed chambers.

FIG. 2 shows a visual apparatus according to the invention, comprising two superimposed chambers 20 and 20a. This visual apparatus is provided with a central tube 21 around which is arranged a fixed sleeve 22, coupled to the tube 21, for example, by spacing devices (not shown.). At the upper part of the fixed sleeve 22 is provided a cavity 22a defined at its lower portion by a flexible diaphragm 22b provided with an orifice 23. At the upper end of the central tube 21 and inside the fixed sleeve 22 is arranged a valve 24 constituted by a needle 25 intended to cooperate with the extremity of the tube 21, forming a seat 21a, and a float 26, the upper part 26a of which can close the orifice 23 of the cavity 22a.

As in the previous construction, this visual apparatus is provided with a perforator 27 and a micro-adjustment device 28. In this construction, the flow of the serum fills the chamber 20, passes between the fixed sleeve 22 and the central tube 21, and acts progressively on the float 26 which rises so as to permit the flow of serum in the channel of the central tube 21 towards the micro-adjustment device 28. The air remains imprisoned at the upper portion of the sleeve 22 in the cavity 22a.

If the level of the serum rises, for example to the level shown at 29, the float 26 is, at that moment, moved upwards against the flexible diaphragm 22b and closes the orifice 23 with its extremity 26a, locking the air in the cavity 22a. In this embodiment, it is impossible for an air-bubble to be conveyed towards the patient.

FIG. 3 shows a transfuser 30 provided with a cylindrical sleeve 31 with its float 32 sliding on a central tube 33. This transfuser is provided with a filter 34. It can readily be seen that the device according to the invention can be advantageously applied to all systems of perfusion-transfusion, thereby avoiding accidents which may especially arise due to the passage of air into the transfused liquid.

FIG. 4 shows an alternative embodiment of the invention, constituted by a chamber 51 forming the visual device and comprising a perforator 52 at its upper portion. Inside the chamber 51 is arranged a fixed central tube 53, on which a sleeve 54 slides freely. The sleeve 54 is made of a material having a suitable density and comprises a central shaft 55. At its base the visual device 51 comprises a micro-adjustment device 56, the central part 57 of which has been extended in such manner as to come into contact with the shaft 55 to lift it. This embodiment has for its main object the advantage of facilitating the priming of the device. When it is desired to prime the apparatus, it is only necessary to screw the micro-adjustment device 56 fully home, so as to lift the sleeve 54, and then introduce the perforator 52 in the receptacle containing the liquid to be transfused. This liquid flows and primes the system and the flow can then be regulated.

FIG. 5 represents another visual apparatus 40 according to the invention comprising a central tube 41 on which is mounted a fixed sleeve 42. Between the upper extremity of the central tube 41 and the top of the fixed sleeve 42 is arranged a ball 43 of synthetic material having a suitable density for the liquid to be perfused. This ball 43 must have a diameter slightly greater than that of the central tube 41, the upper extremity 44 of which forms the seat of the ball 43.

As in the embodiments previously described, the visual device 40 comprises at its upper portion a perforator 45, the channel 46 of which has a notch 47 intended for the free passage of the sterilization gases when the visual apparatus is packed in a hermetically sealed packing. The other extremity of the visual device 40 comprises a micro-adjustment device 48.

In this embodiment, as the sleeve 42 is fixed, it is the ball 43 of plastic material which ensures the stoppage of the flow at the end of the perfusion by coming to rest on its seating 44.

We claim:

1. A system of flow-rate regulation for perfusers-transfusers commonly known as visual apparatus, comprising a chamber of transparent synthetic material having an upper portion provided with a perforator for admission of liquid into said chamber, a fixed central tube in said chamber, said tube having an upper inlet for fluid and a lower outlet for the fluid, a cylindrical sleeve surrounding said tube, float means operatively associated with said sleeve and tube for producing closure of said upper inlet of said tube when liquid in said chamber drops below a predetermined level, said sleeve and tube defining an annular passage therebetween, said sleeve having an open lower end through which liquid is admitted and flows upwardly through said annular passage and then downwardly through said upper inlet in said tube with the latter open when the liquid in the chamber is above said predetermined level as detected by said float means, said cylindrical sleeve being freely slidable on said fixed central tube and including a flexible diaphragm which closes said upper inlet of said tube when the liquid in the chamber drops below said predetermined level and said sleeve having an upper end with a cavity located above said flexible diaphragm.

2. A flow-rate regulator system according to claim 1 wherein said cavity is positioned below the perforator for receiving admitted liquid and for containing the liquid until the cavity is filled whereafter the liquid overflows the cavity and enters the chamber.

3. A flow-rate regulator system according to claim 2 wherein said float means is secured to said sleeve.

4. A flow-rate regulator system according to claim 3, wherein said float means comprises a float constituted by a circular skirt on said sleeve.

5. A flow-rate regulator system according to claim 4, wherein said float is integral with said sleeve and is located at about ⅔' rds of the height of said sleeve.

6. A flow-rate regulator system according to claim 2, wherein said tube has a foot and said sleeve has a lower end which cooperates with said foot to form a seal to prevent entry of liquid into said annular passage when the liquid in said chamber drops below said predetermined level and said diaphragm closes said upper inlet of said tube whereby liquid entry into said tube is blocked at two locations.

7. A flow-rate regulator system according to claim 1, wherein said chamber includes two superimposed chamber portions.

8. A flow-rate regulator system according to claim 1, wherein said sleeve is fixed, said float means comprising a float disposed within said sleeve and including a valve facing said inlet of said tube for closing the inlet when the liquid in said chamber is below said predetermined level.

9. A flow-rate regulator system according to claim 8, wherein said sleeve has a closed upper end, said system further comprising a flexible diaphragm in said sleeve dividing the same into upper and lower cavities, said sleeve being located at a level above said float and being provided with an orifice establishing communication between said cavities, said float including means for closing said orifice when the liquid in said chamber reaches a second predetermined level above the first predetermined level.

10. A flow-rate regulator system according to claim 1, wherein said float means is integrally formed with said sleeve, said sleeve further comprising a projecting shaft, said system further comprising a manually operable control means for adjusting the flow of liquid from the outlet of said tube, said control means facing said projecting shaft for lifting said sleeve during priming of said system.

11. A flow-rate regulator system according to claim 1, comprising a filter in said control tube.

* * * * *